(12) United States Patent
Baugh et al.

(10) Patent No.: US 8,491,851 B2
(45) Date of Patent: Jul. 23, 2013

(54) SYSTEM AND METHOD FOR ENABLING AND DISABLING A PORTABLE ASSAY READER DEVICE

(75) Inventors: Brenton A. Baugh, Palo Alto, CA (US); Robert Sean Murphy, Sunnyvale, CA (US)

(73) Assignee: Alverix, Inc., San Jose, CA (US)

( * ) Notice: Subject to any disclaimer, the term of this patent is extended or adjusted under 35 U.S.C. 154(b) by 774 days.

(21) Appl. No.: 11/607,352

(22) Filed: Nov. 30, 2006

(65) Prior Publication Data

US 2008/0131321 A1 Jun. 5, 2008

Related U.S. Application Data

(60) Provisional application No. 60/840,157, filed on Aug. 25, 2006.

(51) Int. Cl.
*G01N 21/75* (2006.01)

(52) U.S. Cl.
USPC ........... 422/402; 422/400; 422/401; 422/420; 422/421; 422/422; 422/423; 422/424; 422/425; 422/426; 422/427; 422/428; 422/429; 422/68.1; 422/82.05; 422/82.06; 422/500; 422/557; 422/559; 422/560; 422/561; 436/164; 436/169; 436/170; 435/13; 435/283.1; 435/287.1; 435/287.7; 435/287.8; 435/287.9; 435/288.7

(58) Field of Classification Search
USPC .................. 422/68.1, 82.05–82.08, 401, 402, 422/420, 500, 557, 559, 560, 561, 400, 421, 422/422, 423, 424, 425, 426, 427, 428, 429, 82.06; 436/164, 169, 170; 435/13, 283.1, 435/287.1, 287.7, 287.8, 287.9, 288.7
See application file for complete search history.

(56) References Cited

U.S. PATENT DOCUMENTS

| | | | |
|---|---|---|---|
| 5,952,634 A * | 9/1999 | Yoshida | 200/302.2 |
| 6,342,183 B1 | 1/2002 | Lappe et al. | |
| 6,623,979 B2 | 9/2003 | Lappe et al. | |
| 6,716,393 B2 | 4/2004 | Lappe et al. | |
| 2002/0170823 A1 * | 11/2002 | Housefield et al. | 204/403.01 |
| 2005/0196318 A1 * | 9/2005 | Matusewicz et al. | 422/58 |
| 2007/0143035 A1 * | 6/2007 | Petruno | 702/27 |

* cited by examiner

*Primary Examiner* — Dennis M White
(74) *Attorney, Agent, or Firm* — K&L Gates LLP

(57) ABSTRACT

A detection system in a portable assay reader device is enabled or activated after a user applies a manual force to a portion of the reader device, to an object supporting the assay test strip, or to the assay test strip itself. The movement moves a switch from an open state to a closed state. The closed state enables a detection system to monitor one or more test regions in the assay test strip for a reaction. The detection system can include one or more imagers, one or more electrical detectors, one or more magnetic detectors, or one or more optical detectors that monitor the one or more test regions for applicable visible, electrical, magnetic, or optical reactions, respectively. The one or more imagers or detectors transmit data to a processing device to determine the results of a test.

20 Claims, 6 Drawing Sheets

SYSTEM AND METHOD FOR ENABLING AND DISABLING A PORTABLE ASSAY READER DEVICE

CROSS REFERENCE TO RELATED APPLICATIONS

This application claims the benefit of U.S. Provisional Application No. 60/840,157, filed on Aug. 25, 2006.

BACKGROUND

Lateral flow assays and other types of calorimetric assays are used for a variety of diagnostic tests, including food safety tests, water quality tests, and medical tests such as home pregnancy and drug tests. Some diagnostic tests, such as drug tests, typically involve an initial screening test to identify those samples that test positive for the presence of drugs or particular chemical components. A confirmation test is then performed on the samples that test positive to identify the specific drug or chemical components present in the sample.

Usually screening tests are performed locally and confirmation tests performed at a centralized laboratory. For example, a drug screening test can be performed on potential or current employees at an employer work site or local doctor's office and the confirmation tests performed at a centralized medical laboratory. U.S. Pat. No. 6,716,393 by Lappe et al. discloses a test system for automatic testing of fluid samples. An assaying device includes a collection cup and a cap that visibly houses at least one test strip. The collection cup stores the fluid sample to be tested. An electrically-powered reader device applies a downward force to a piston and plunger element in order to deliver an aliquot from the fluid sample to the one or more test strips. Included in the reader device are a camera and a processor. The camera captures images of the one or more visible test strips and the processor analyzes the captured images to determine the results of the test.

Although the system described in U.S. Pat. No. 6,716,393 provides an automatic method for testing fluid samples, the system is limited in its portability. The size and weight of the assay reader device can limit is use in the field. Moreover, the assay reader device must be located near a source of electrical power in order to perform and complete the tests.

SUMMARY

In accordance with the invention, a system and method for enabling and disabling a portable assay reader device are provided. A detection system in a portable assay reader device is enabled or activated after a user applies a manual force to a portion of the reader device, to an object supporting the assay test strip, or to the assay test strip itself. The movement moves a switch from an open state to a closed state. The closed state enables a detection system to monitor one or more test regions in the assay test strip for a reaction. The detection system can include one or more imagers, one or more electrical detectors, one or more magnetic detectors, or one or more optical detectors that monitor the one or more test regions for applicable visible, electrical, magnetic, or optical reactions, respectively. The one or more imagers or detectors transmit data to a processing device to determine the results of a test.

DETAILED DESCRIPTION

Figure 1:
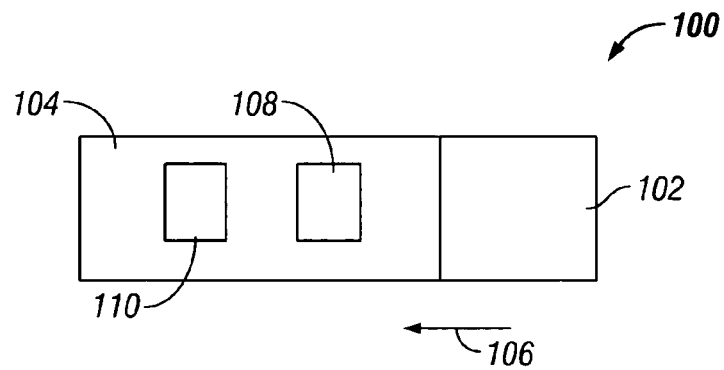
FIG. 1 is a top view of a lateral flow assay test strip that can be used with embodiments of the invention.

The following description is presented to enable embodiments of the invention to be made and used, and is provided in the context of a patent application and its requirements. Various modifications to the disclosed embodiments will be readily apparent, and the generic principles herein may be applied to other embodiments. Thus, the invention is not intended to be limited to the embodiments shown but is to be accorded the widest scope consistent with the appended claims. Like reference numerals designate corresponding parts throughout the figures.

Referring now to FIG. 1, there is shown a graphic illustration of a top view of a lateral flow assay test strip that can be used with embodiments of the invention. Lateral flow assay 100 includes wick region 102 and detection region 104. A holding region (not shown) may be included with assay 100 in order to hold assay 100 when applying a liquid test sample to wick region 102 or when examining assay 100 to determine the results.

Wick region 102 is used to introduce a liquid test sample to assay 100. Wick region 102 and detection region 104 are typically made of a porous material. When a liquid test sample is applied to wick region 102, wick region 102 conveys the liquid by capillary action into detection region 104, as indicated by arrow 106. The liquid test sample may be received by wick region 102, for example, by dipping wick region 102 into the liquid test sample or by dropping samples of the liquid test sample onto wick region 102.

Detection region 104 typically includes test region 108 and control band 110. Control band 110 is used to indicate the liquid test sample is successfully conveyed through test region 108. Test region 108 reacts to the liquid test sample when a given chemical compound or molecule is present in the liquid test sample. By way of example only, test region 108 can change color or produce fluorescence when one or more compounds or molecules are present in the liquid test sample. The presence or absence of a reaction in test region 108 is used to determine the results of a particular test.

Figure 2A:
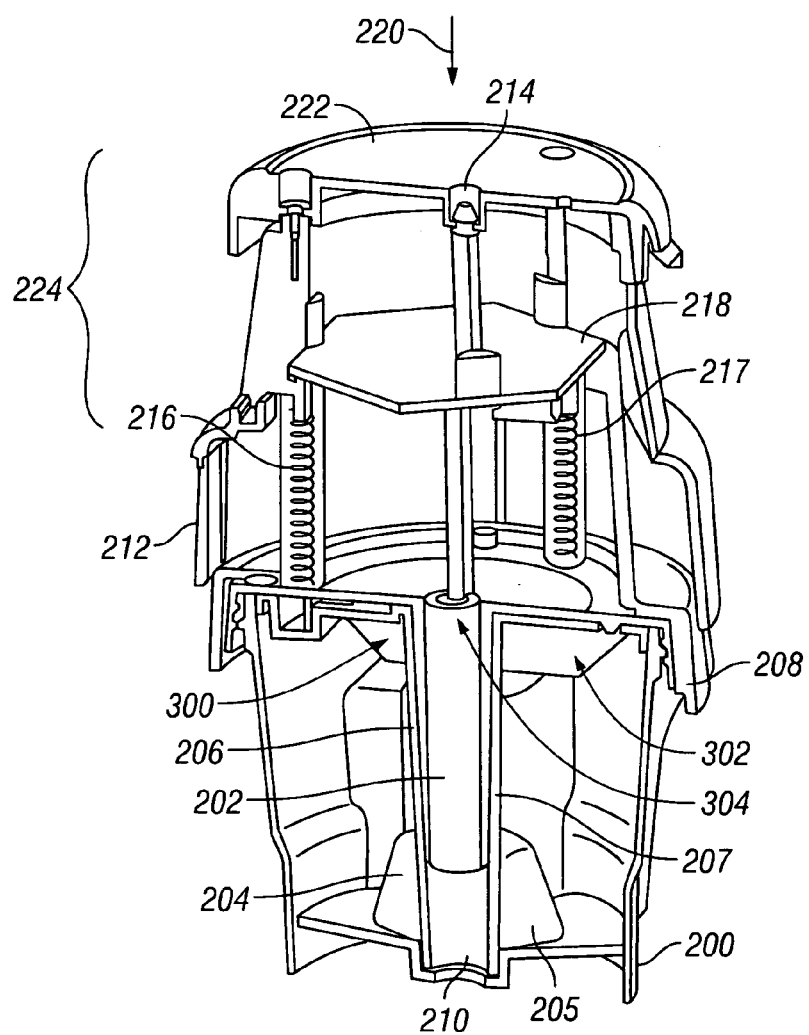
FIGS. 2A-2B depict cross-sectional views of portions of a collection cup and a first assay reader device in an embodiment in accordance with the invention.
Figure 2B:
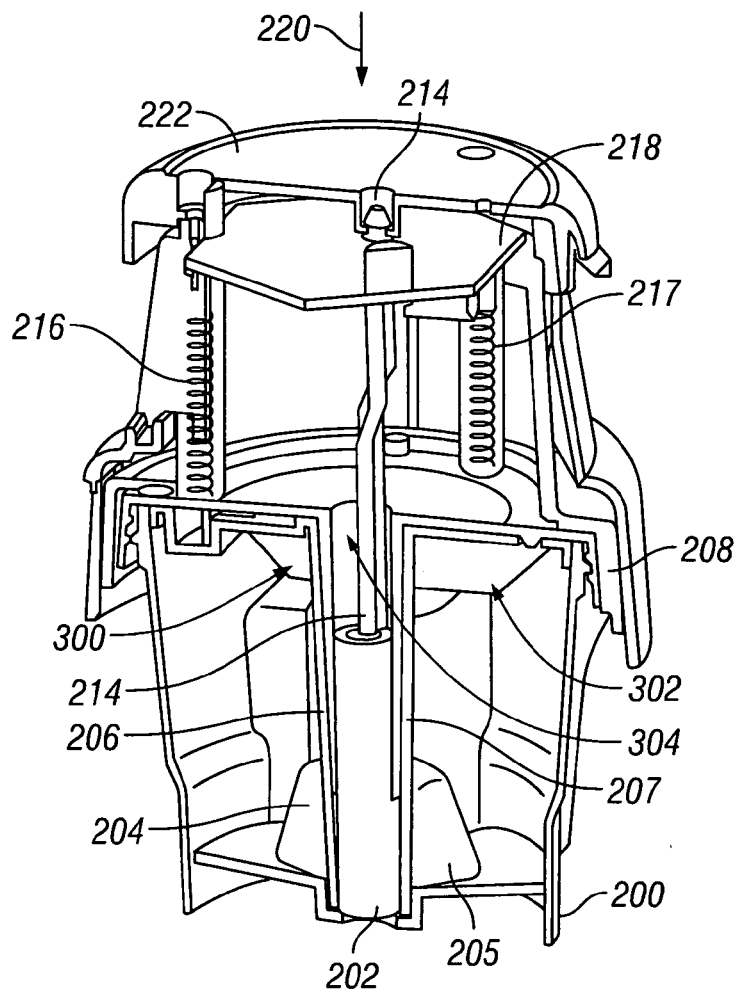

Referring now to FIG. 2A, there is shown a cross-sectional view of a portion of a collection cup and a first assay reader device in an embodiment in accordance with the invention. The assay reader device shown in FIGS. 2A-2B is designed to operate in combination with a collection cup manufactured by eScreen, Inc. located in Overland Park, Kans. Only those components in the collection cup necessary to understand the invention are shown in FIG. 2. A more detailed description of the collection cup is disclosed in U.S. Pat. Nos. 6,342,183 and 6,623,979, both by Lappe et al.

Figure 3:
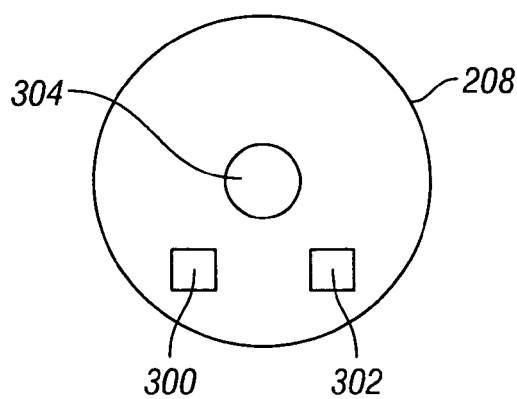
FIG. 3 illustrates a top view of lid 208 shown in FIG. 2.

Collection cup 200 includes plunger 202, side walls 204, 205, passageways 206, 207, and lid 208. A top view of lid 208 is shown in FIG. 3. Lid 208 includes visible assay test strips 300, 302 and opening 304. Side walls 204, 205 are configured to form well 210. A liquid test sample is contained in cup 200 such that a portion of the sample resides in well 210.

Assay reader device 212 includes plunger 214, spring assemblies 216, 217, and detection system 218. Reader device 212 removably attaches to lid 208 of collection cup 200. By way of example only, reader device 212 removably screws onto lid 208 in an embodiment in accordance with the invention.

When a test is to be performed on a liquid test sample, the top of plunger 202 in collection cup 200 is positioned in opening 304 (see FIG. 3). Reader device 212 is then attached to lid 208 and plunger 214 positioned above opening 304. To begin the test, a user manually applies a downward force (see arrow 220) to the top surface 222 of reader device 212. The downward force causes a sliding mechanism, in this embodiment the upper portion 224 of reader device 212 and spring assemblies 216, 217, to move and compress spring assemblies 216, 217. This downward movement moves plunger 214 into opening 304 such that plunger 214 makes contact with plunger 202.

As the user continues to apply a downward force to the top surface 222 of reader device 212, plunger 214 pushes plunger 202 into well 210 until plunger 202 rests on the bottom surface of well 210 (see FIG. 2B). As plunger 202 moves into well 210, the liquid test sample in well 210 is displaced and forced into passageways 206, 207. Passageways 206, 207 convey the liquid test sample to assay test strips 300, 302. Detection system 218 is positioned above assay test strips 300, 302 and detects any visible reactions in assay test strips 300, 302.

Figure 4:
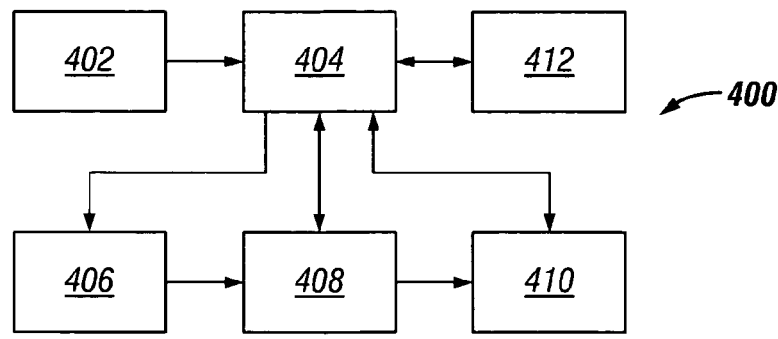
FIG. 4 depicts a simplified block diagram of a portion of a detection system in an embodiment in accordance with the invention.

Referring now to FIG. 4, there is shown a simplified block diagram of a portion of a detection system in an embodiment in accordance with the invention. Detection system 400 includes switch assembly 402, controller 404, imager 406, memory 408, processor 410, and input/output 412. Imager 406 captures one or more images of assay test strips 300, 302 in response to switch assembly 402 being placed in a closed state. Switch assembly 402 is described in more detail in conjunction with FIG. 5.

The one or more images are stored in optional memory 408 before processor 410 analyzes the images to determine the presence or absence of a visible reaction in assay test strips 300, 302. Processor 410 transmits test results data to controller 404 in an embodiment in accordance with the invention. In other embodiments in accordance with the invention, processor 410 and controller 404 are implemented as one processing device.

Upon receipt of the test results, controller 404 transmits the test results data to input/output 412. Input/output 412 then transmit the test results to an output device, such as a display or printer (not shown) in an embodiment in accordance with the invention. In another embodiment in accordance with the invention, input/output 412 transmit the test result data to a computing device, such as a laptop computer (not shown).

Although the embodiment shown in FIG. 4 has been described in conjunction with an imager, other embodiments are not limited to this implementation. Imager 406 can be replaced with a different type of detector, such as an electrical, magnetic, or optical detector. The detector monitors a test region in an assay test strip for electrical, magnetic, or optical reactions, respectively. By way of example only, the electrical reaction can include resistive or capacitance changes, the magnetic reaction can include a change in a magnetic field surrounding the test region, and the optical reaction can include the production of fluorescence or luminescence.

Figure 5A:
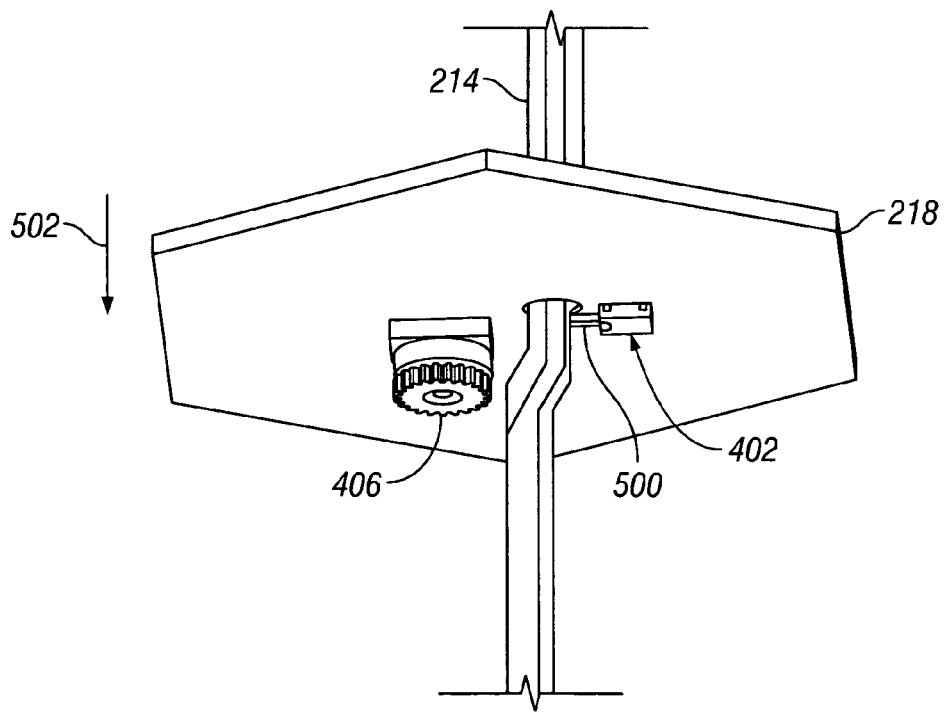
FIGS. 5A-5B illustrate bottom perspective views of detection system 218 shown in FIG. 2.

Referring now to FIG. 5A, there is shown a bottom perspective view of detection system 218. FIG. 5A illustrates switch assembly 402 in an open state and plunger 214. The open state occurs when a user is ready to perform a test but has not yet manually applied a downward force to the top surface 222 of assay reader device 212.

Detection system 218 is implemented on a printed circuit board in an embodiment in accordance with the invention. Switch assembly 402 and imager 406 are affixed or mounted to the printed circuit board opposite the test strips 300, 302 in an embodiment in accordance with the invention. Switch assembly 402 includes switch 500. Plunger 214 moves in a direction indicated by arrow 502 when a user manually applies a downward force to the top surface 222 of reader device 212. An upper notch 504 (see FIG. 5B) in cutout region 506 in plunger 214 moves switch 500 to a closed state as plunger 214 moves downward. The closed state enables detection system 218 to begin monitoring assay test strips 300, 302 for any visible reactions.

When a user stops applying a downward force to the top surface 222 of reader device 212, plunger 214 moves upward or returns to a resting position and switch 500 returns to an open state. When switch 500 returns to the open state, detection system 218 is disabled and stops monitoring assay test strips 300, 302 in an embodiment in accordance with the invention. In another embodiment in accordance with the invention, a timer or clock (not shown) allows detection system to continue monitoring assay test strips 300, 302 for a fixed amount of time after switch 500 is returned to the open state.

Figure 5B:
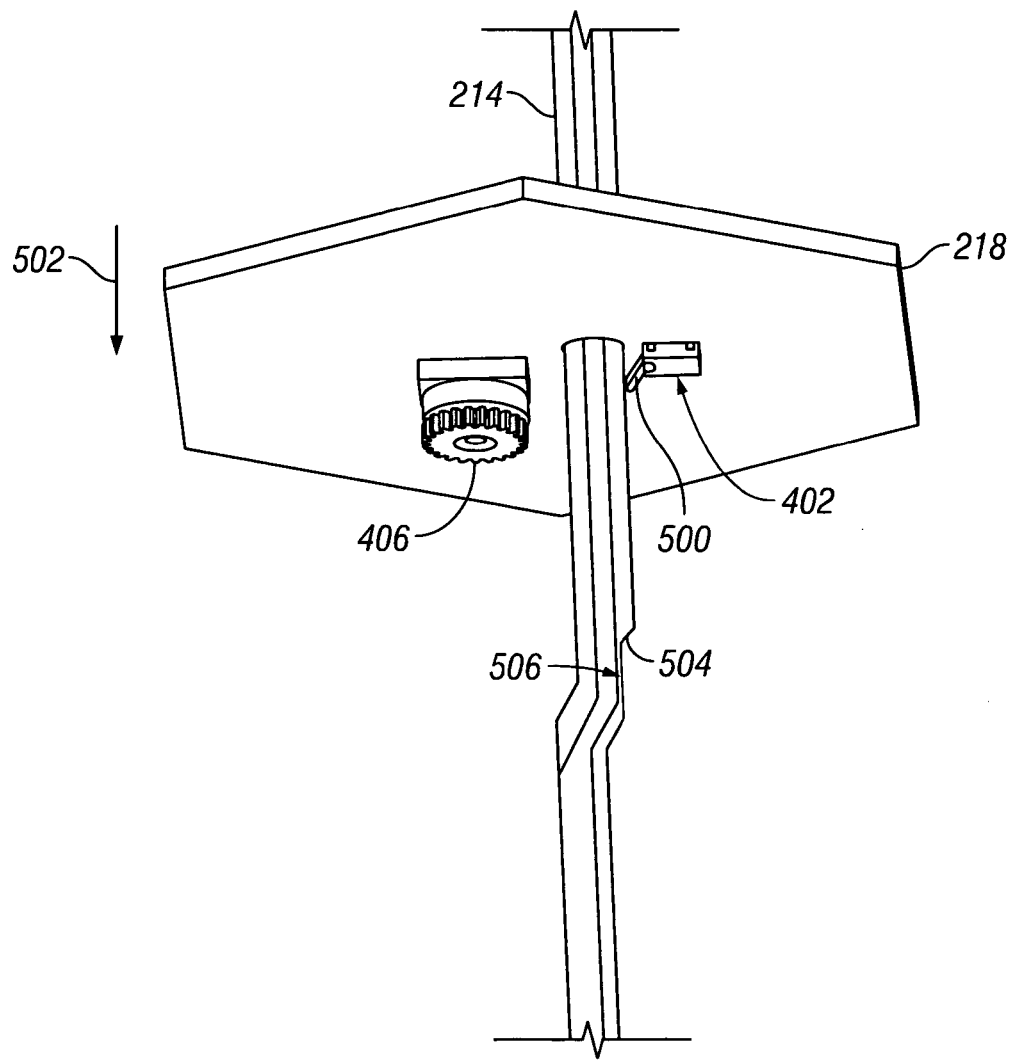

In the embodiment shown in FIG. 5B, switch 500 is implemented as a spring-loaded switch that automatically returns to the open state when plunger 214 returns to a resting position. Embodiments in accordance with the invention, however, are not limited to this construction. Other embodiments can return switch 500 to the open state using different techniques. By way of example only, cutout region 506 is implemented in a "U" shape such that notch 504 moves switch 500 to a closed state and the opposing notch of the "U" shape returns switch 500 to the open state.

Figure 6:
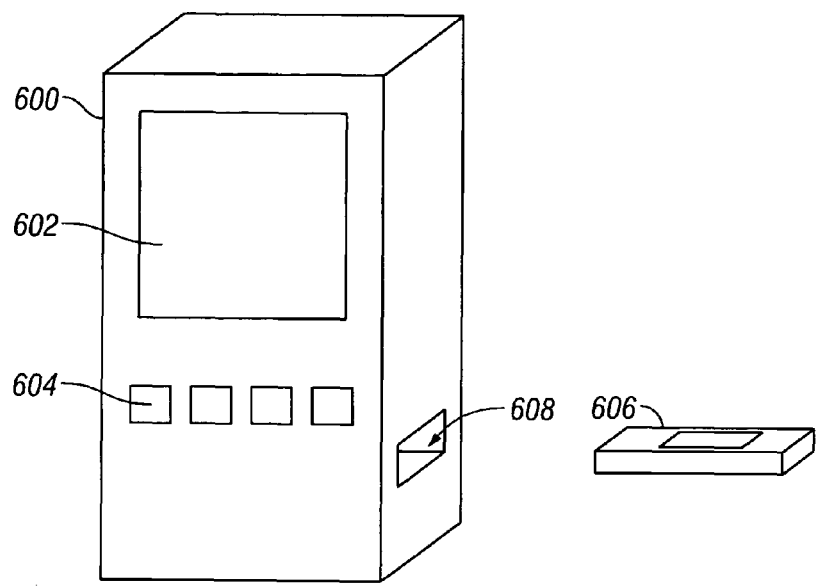
FIG. 6 is a perspective view of a second assay reader device in an embodiment in accordance with the invention.

FIG. 6 is a perspective view of a second assay reader device in an embodiment in accordance with the invention. Reader device 600 includes display 602 and one or more selection or input buttons 604. Assay test strip 606 is manually inserted into opening 608 when a test is to be performed. Assay test strip 606 is supported by moveable tray 700 as assay test strip 606 is inserted into opening 608 (see FIG. 7A).

Figure 7A:
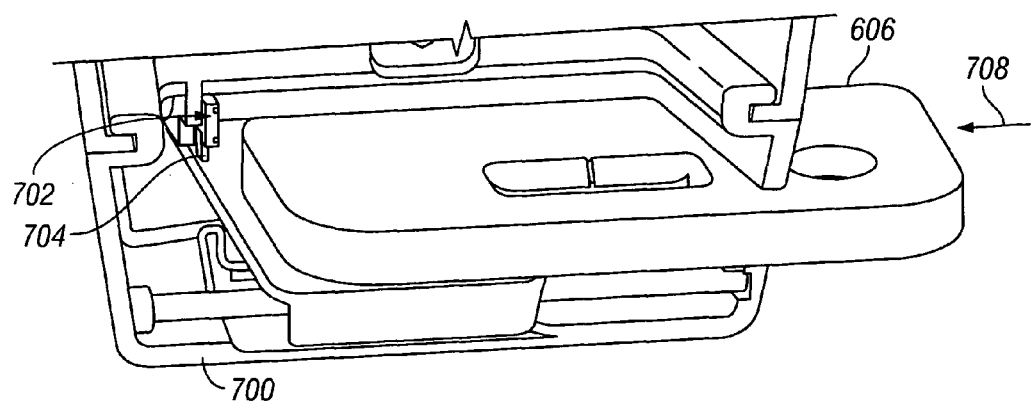
FIG. 7A illustrates switch 500 in an open state with assay test strip 606 only partially inserted into opening 706 shown in FIG. 6.

Switch assembly 702 is positioned in the embodiment shown in FIG. 7A so that switch 704 moves from an open state to a closed state in response to a manual force applied in the direction indicated by arrow 708 to a sliding mechanism implemented as assay test strip 606 and moveable tray 700. FIG. 7A illustrates switch 704 in an open state with assay test strip 606 only partially inserted into opening 608.

Figure 7B:
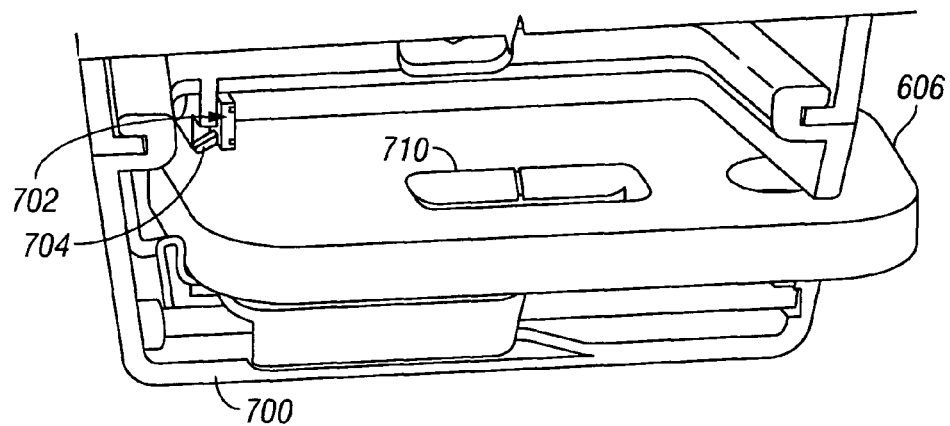
FIG. 7B depicts switch 600 in a closed state and assay test strip 606 inserted completely into opening 706 shown in FIG. 6.

FIG. 7B depicts switch 704 in a closed state and assay test strip 606 inserted completely into opening 608. The closed state enables a detection system (not shown) to begin monitoring test region 710 for any reactions. Switch 704 is returned to the open state when assay test strip 606 is removed from opening 608. Switch 704 is implemented as a spring-loaded switch that automatically returns to the open state when assay test strip 606 is removed from reader 600. Other embodiments in accordance with the invention can use different techniques to move switch 704 between open and closed states, such as, for example, a notch or depression formed in the end of assay test strip 606.

Figure 8:
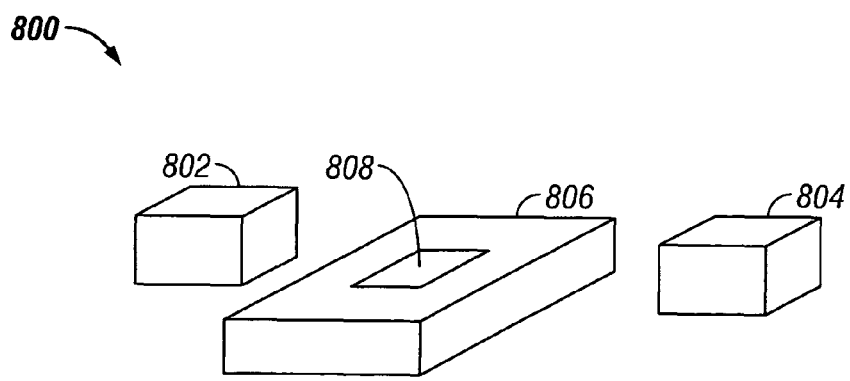
FIG. 8 is a simplified block diagram of a switch system in an embodiment in accordance with the invention.

Embodiments in accordance with the invention are not limited to a switch assembly as described in conjunction with FIGS. 5-7. Other types of switches may be used in other embodiments in accordance with the invention. FIG. 8 is a simplified block diagram of a switch system in an embodiment in accordance with the invention. Switch system 800 includes detectors 802, 804. Embodiments in accordance with the invention can use one detector or both detectors, depending on the type of reaction produced by test region 808 of assay 806.

A user applies a manual force to a sliding mechanism that includes assay test strip 806 to move assay test strip 806 into a position that allows detectors 802, 804 to monitor test region 808. By way of example only, a moveable tray is used to move assay test strip 806. In one embodiment in accordance with the invention, one or both of the detectors 802, 804 are electrical detectors that monitor test region 808 for an electrical reaction. By way of example only, the electrical reaction can be a capacitance or resistive change in test region 808 when the presence of a target molecule or microorganism is detected in the liquid test sample. The electrical reaction acts as a switch that enables or activates a detection system (not shown). The detector or detectors 802, 804 transmit data to the detection system that enables the detection system to analyze the data and determine the results of a test in an embodiment in accordance with the invention.

In another embodiment in accordance with the invention, one or both of the detectors 802, 804 are magnetic detectors that monitor test region 808 for a magnetic reaction. By way of example only, the magnetic reaction produces a change in a magnetic field in test region 808 when the presence of a target molecule or microorganism is detected in the liquid test sample. The magnetic reaction acts as a switch that enables or activates a detection system. The detector or detectors 802, 804 transmit data to the detection system that enables the detection system to analyze the data and determine the results of a test in an embodiment in accordance with the invention.

And in yet another embodiment in accordance with the invention, one or both of the detectors 802, 804 are optical detectors that monitor test region 808 for an optical reaction. By way of example only, test region 808 may emit fluorescence or luminescence when the presence of a target molecule or microorganism is detected in the liquid test sample. Detection of the fluorescence or luminescence an imager or detector array can act as a switch that enables or activates a detection system. The detector or detectors 802, 804 transmit data to the detection system that enables the detection system to analyze the data and determine the results of a test in an embodiment in accordance with the invention.

The invention claimed is:

1. An assay reader device, comprising:
    a sliding mechanism adapted to move in response to a manual force applied by a user directly to a top surface of the reader device and displace a liquid test sample into passageways that convey the liquid test sample to an assay test strip, wherein the top surface of the reader device is opposite an end of the reader device that attaches to a lid of a collection cup;
    a detection system adapted to detect a reaction in a test region in the assay test strip;
    a switch adapted to move in response to a movement of the sliding mechanism, wherein the switch enables the detection system when the switch is moved to a first position.

2. The assay reader device of claim 1, wherein the detection system comprises:
    an imager operable to capture one or more images of the reactive test region in the assay test strip; and
    a processing device operable to analyze the one or more images received from the imager.

3. The assay reader device of claim 1, wherein the detection system comprises one of an electrical detector, a magnetic detector, and an optical detector.

4. The assay reader device of claim 1, wherein the switch disables the detection system when the switch is moved a second position.

5. The assay reader device of claim 1, further comprising a memory operable to store the one or more images.

6. The assay reader device of claim 1, wherein the sliding mechanism comprises a tray operable to support the assay test strip.

7. The assay reader device of claim 6, wherein the switch is positioned adjacent to the tray such that a movement of the tray produces a movement of the switch.

8. The assay reader device of claim 1, wherein the sliding mechanism comprises a moveable surface connected to a plunger and positioned parallel to the assay test strip.

9. The assay reader of claim 8, wherein the plunger is positioned perpendicular to the moveable surface.

10. The assay reader device of claim 9, wherein the switch is positioned adjacent to the plunger such that a movement of moveable surface produces a movement of the plunger resulting in a movement of the switch.

11. An assay reader device, comprising:
    a sliding mechanism that moves in response to a manual force applied by a user directly to a top surface of the reader device and displace a liquid test sample into passageways that convey the liquid test sample to an assay test strip, wherein the top surface of the reader device is opposite an end of the reader device that attaches to a lid of a collection cup; and
    one or more detectors each adapted to detect a reaction in a test region of the assay test strip, wherein the one or more detectors are adapted to enable a detection system in response to detecting a reaction in the test region.

12. The assay reader device of claim 11, wherein the one or more detectors comprise one or more electrical detectors each operable to detect an electrical reaction in the test region in the assay test strip.

13. The assay reader device of claim 11, wherein the one or more detectors comprise one or more magnetic detectors each operable to detect a magnetic reaction in the test region in the assay test strip.

14. The assay reader device of claim 11, wherein the one or more detectors comprise one or more optical detectors each operable to detect an optical reaction in the test region in the assay test strip.

15. A method for fabricating an assay reader device, the method comprising:
    providing a sliding mechanism adapted to move in response to a manual force applied by a user directly to a top surface of the reader device and displace a liquid test sample into passageways that convey the liquid test sample to an assay test strip, wherein the top surface of the reader device is opposite an end of the reader device that attaches to a lid of a collection cup;
    positioning a switch such that a movement of the sliding mechanism produces a movement of the switch; and providing a detection system adapted to detect a reaction in a test region in the assay test strip, wherein the switch enables the detection system when the switch is moved to a first position.

16. The method of claim 15, wherein providing a detection system operable to detect a reaction in a test region in an assay test strip comprises:
   positioning an imager operable to capture one or more images of the test region in the assay test strip; and
   providing a processing device operable to analyze the one or more images received from the imager.

17. The method of claim 15, wherein providing a detection system operable to detect a reaction in a test region in an assay test strip comprises providing an electrical detection system operable to detect an electrical reaction in the test region in the assay test strip.

18. The method of claim 15, wherein providing a detection system operable to detect a reaction in a test region in an assay test strip comprises providing a magnetic detection system operable to detect a magnetic reaction in the test region in the assay test strip.

19. The method of claim 15, wherein providing a sliding mechanism operable to move in response to a manual force applied by a user comprises providing a tray operable to support the test region in the assay test strip and operable to move in response to a manual force applied by a user.

20. The method of claim 15, wherein providing a sliding mechanism operable to move in response to a manual force applied by a user comprises providing moveable surface connected to a plunger and positioning the switch adjacent to the plunger such that a movement of the surface produces a movement of the plunger resulting in a movement of the switch.

* * * * *

UNITED STATES PATENT AND TRADEMARK OFFICE
CERTIFICATE OF CORRECTION

| | | |
|---|---|---|
| PATENT NO. | : 8,491,851 B2 | Page 1 of 1 |
| APPLICATION NO. | : 11/607352 | |
| DATED | : July 23, 2013 | |
| INVENTOR(S) | : Baugh et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 886 days.

Signed and Sealed this
Twenty-first Day of July, 2015

Michelle K. Lee
*Director of the United States Patent and Trademark Office*